United States Patent
Sheshbaradaran et al.

(10) Patent No.: US 9,089,578 B2
(45) Date of Patent: Jul. 28, 2015

(54) METHOD OF TREATING NEUROENDOCRINE TUMORS

(71) Applicant: Niiki Pharma Acquisition Corp. 2, Tampa, FL (US)

(72) Inventors: Hooshmand Sheshbaradaran, Hoboken, NJ (US); William McCulloch, Hoboken, NJ (US)

(73) Assignee: Intezyne Technologies, Inc., Tampa, FL (US)

( * ) Notice: Subject to any disclaimer, the term of this patent is extended or adjusted under 35 U.S.C. 154(b) by 0 days.

(21) Appl. No.: 13/869,975

(22) Filed: Apr. 25, 2013

(65) Prior Publication Data

US 2013/0237510 A1    Sep. 12, 2013

Related U.S. Application Data

(63) Continuation of application No. PCT/US2011/057555, filed on Oct. 25, 2011.

(60) Provisional application No. 61/406,565, filed on Oct. 25, 2010, provisional application No. 61/508,699, filed on Jul. 18, 2011.

(51) Int. Cl.
| | |
|---|---|
| *A61K 31/416* | (2006.01) |
| *A61K 33/24* | (2006.01) |
| *A61K 31/555* | (2006.01) |
| *A61K 31/4545* | (2006.01) |
| *A61K 31/7068* | (2006.01) |
| *A61K 45/06* | (2006.01) |

(52) U.S. Cl.
CPC .......... *A61K 31/555* (2013.01); *A61K 31/4545* (2013.01); *A61K 31/7068* (2013.01); *A61K 33/24* (2013.01); *A61K 45/06* (2013.01)

(58) Field of Classification Search
None
See application file for complete search history.

(56) References Cited

U.S. PATENT DOCUMENTS 7,338,946 B2 *  3/2008  Keppler ................ 514/184

OTHER PUBLICATIONS

U.S. Appl. No. 13/493,922, filed Jun. 2012, Sheshbaradaran.*
U.S. Appl. No. 13/657,888, filed Oct. 2012, Sheshbaradaran.*
U.S. Appl. No. 13/663,438, filed Oct. 2012, Sheshbaradaran.*
U.S. Appl. No. 13/743,356, filed Jan. 2013, Sheshbaradaran.*
U.S. Appl. No. 13/869,975, filed May 2013, Sheshbaradaran.*
U.S. Appl. No. 13/896,344, filed May 2013, Sheshbaradaran.*
U.S. Appl. No. 13/744,423, filed Jan. 2013, Sheshbaradaran.*
U.S. Appl. No. 13/655,477, filed Oct. 2012, Sheshbaradaran.*
U.S. Appl. No. 13/964,287, filed Aug. 2013, Sheshbaradaran.*
U.S. Appl. No. 13/974,958, filed Aug. 2013, Sheshbaradaran.*
U.S. Appl. No. 14/117,456, filed Nov. 2013, Sheshbaradaran.*
Kapitza et al., "Heterocyclic Complexes of Ruthenium (III) Induce Apopotosis in Colorectal Carcinoma Cells," J. Cancer Res. Clin. Oncol. (2005) 131: 101-110.*
Morbidelli et al., "Antiangiogenic Properties of Selected Ruthenium III Complexes That Are Nitric Oxide Scavenger," British Journal of Cancer (2003) 88, 1484-1491.*
Feng et al., Expression of p53, inducible nitric oxide synthase and vascular endothelial growth factor in gastric precancerous and cancerous lesions: correlation with clinical features. BMC Cancer. 2002;2:8.*
Hartinger, J of Inorganic Biochemistry 100 (2006) 891-904.*
Yao, J. Clin. Oncol. 26: 3063-3072, 2008.*

* cited by examiner

*Primary Examiner* — Svetlana M Ivanova
(74) *Attorney, Agent, or Firm* — Kevin N. Sill

(57) ABSTRACT

Methods and compositions for treating neuroendocrine tumors are disclosed.

9 Claims, No Drawings

METHOD OF TREATING NEUROENDOCRINE TUMORS

RELATED APPLICATIONS

This application is a continuation of PCT/US2011/057555 filed on Oct. 25, 2011, which is entitled to the priority of U.S. Provisional Application No. 61/406,565 filed on Oct. 25, 2010, and U.S. Provisional Application No. 61/508,699 filed on Jul. 18, 2011, the entire content of both of which being incorporated herein by reference.

FIELD OF THE INVENTION

The present invention generally relates to pharmaceutical compositions and methods for treating cancer, and particularly to a pharmaceutical composition having a ruthenium (III) complex, and method of using thereof.

BACKGROUND OF THE INVENTION

Neuroendocrine tumors (NETs) are tumors arising from cells of the endocrine and nervous systems. Although there are many types of NETs, they share common features. For example, the cells of these neoplasms all have special secretory granules. They also often secrete biogenic amines or polypeptide hormones. The prevalence NETs is estimated to be 35 per 100,000. See Öberg & Castellano, *Cancer and Metastasis Reviews* 30:3-7 (2011). Somatostatin analogs such as Octreotide LAR are often used. But they only alleviate symptoms by blocking hormone release. Chemotherapies with cisplatin, etoposide and doxorubicin are often administered, but with only marginal effect. Thus, there is still significant need for additional pharmaceuticals and methods for treating NETs.

SUMMARY OF THE INVENTION

The present invention provides methods of treating neuroendocrine tumors. In one aspect, the present invention provides a method of treating, preventing, or delaying the onset of, neuroendocrine tumors, comprising administering to a patient having a neuroendocrine tumor a therapeutically or prophylactically effective amount of a pharmaceutically acceptable salt of trans-[tetrachlorobis(1H-indazole)ruthenate(III)] (e.g., sodium trans-[tetrachlorobis(1H-indazole)ruthenate(III)] or potassium trans-[tetrachlorobis(1H-indazole)ruthenate(III)]).

In accordance with another aspect, a method of treating, preventing, or delaying the onset of, a refractory neuroendocrine tumor is provided comprising administering a therapeutically or prophylactically effective amount of a pharmaceutically acceptable salt of trans-[tetrachlorobis(1H-indazole)ruthenate(III)] (e.g., sodium trans-[tetrachlorobis(1H-indazole)ruthenate(III)] or potassium trans-[tetrachlorobis(1H-indazole)ruthenate(III)]) to a patient having refractory neuroendocrine tumor.

Use of a pharmaceutically acceptable salt of trans-[tetrachlorobis(1H-indazole)ruthenate(III)] (e.g., sodium trans-[tetrachlorobis(1H-indazole)ruthenate(III)] or potassium trans-[tetrachlorobis(1H-indazole)ruthenate(III)]) for the manufacture of a medicament for use in the methods of the present invention is also provided.

The foregoing and other advantages and features of the invention, and the manner in which the same are accomplished, will become more readily apparent upon consideration of the following detailed description of the invention taken in conjunction with the accompanying examples, which illustrate preferred and exemplary embodiments.

DETAILED DESCRIPTION OF THE INVENTION

The present invention is at least in part based on the discovery that the compound sodium trans-[tetrachlorobis(1H-indazole)ruthenate(III)] is particularly effective in treating neuroendocrine tumors (NET). Accordingly, in accordance with a first aspect of the present invention, a method is provided for treating neuroendocrine tumors including primary and metastatic neuroendocrine tumors. The method comprises treating a patient having one or more neuroendocrine tumors in need of treatment with a therapeutically effective amount of trans-[tetrachlorobis(1H-indazole)ruthenate(III)] or a pharmaceutically acceptable salt thereof. Examples of such a salt include an indazolium salt or alkali metal salt of trans-[tetrachlorobis(1H-indazole)ruthenate(III)] (e.g., sodium trans-[tetrachlorobis(1H-indazole)ruthenate(III)] or potassium trans-[tetrachlorobis(1H-indazole)ruthenate(III)]). That is, the present invention is directed to the use of an effective amount of a trans-[tetrachlorobis(1H-indazole)ruthenate(III)] or a pharmaceutically acceptable salt thereof (e.g., indazolium or alkali metal salt) for the manufacture of medicaments for treating a neuroendocrine tumor in patients identified or diagnosed as having a neuroendocrine tumor.

Neuroendocrine tumors are tumors originated from endocrine glands such as adrenal medulla, pituitary, and parathyroids, or from endocrine islets within thyroid or pancreas, or from dispersed endocrine cells in the respiratory and gastrointestinal tract. They are typically characterized with the presence of secretory granules and the ability to produce hormones or biogenic amines. In various embodiments, the neuroendocrine tumors treated in the present invention may be carcinoid tumors (e.g., bronchial carcinoids, gastric carcinoids, small intestine carcinoids, appendeceal carcinoids, and rectal carcinoids) and pancreatic neuroendocrine tumors (e.g., insulinoma, glucagonoma, VIPoma, somatostatinoma, and PPoma etc.). In some embodiments, the method of the present invention is used to treat carcinoid syndrome. In some embodiments, the method of the present invention is used to treat gastrointestinal neuroendocrine tumors. In some embodiments, the method of the present invention is used to treat gastrinoma, either of duodenum or pancreas. In some specific embodiments, the method of the present invention is used to treat Zollinger-Ellison syndrome. In some embodiments, the method of the present invention is used to treat thyroid carcinoma or Merkel cell carcinoma of the skin. In some embodiments, the method of the present invention is used to treat neuroendocrine tumor of the anterior pituitary, medullary carcinoma, parathyroid tumors, thymus and mediastinal carcinoid tumors, pulmonary neuroendocrine tumors, gastroenteropancreatic neuroendocrine tumors, adrenomedullary tumors, pheochromocytoma, Schwannoma, paraganglioma, neuroblastoma, urinary tract carcinoid tumor and neuroendocrine carcinoma, multiple endocrine neoplasia type 1 (MEN1), multiple endocrine neoplasia type 2 (MEN2), von Hippel-Lindau (VHL) disease, neurofibromatosis type 1, tuberous sclerosis, or Carney complex.

In the various embodiments of this aspect of the present invention, the treatment method optionally also comprises a step of diagnosing or identifying a patient as having neuroendocrine tumor. The identified patient is then treated with or administered with a therapeutically effective amount of trans-[tetrachlorobis(1H-indazole)ruthenate(III)] or a pharmaceutically acceptable salt thereof, preferably an alkali metal salt, e.g., sodium trans-[tetrachlorobis(1H-indazole)ruthenate (III)]. Various neuroendocrine tumors may be diagnosed in any conventional diagnostic methods known in the art such as CT scan, endoscopy, biopsy, etc.

In addition, another aspect of the present invention provides a method of treating refractory neuroendocrine tumor comprising treating a patient identified as having a refractory neuroendocrine tumor with a therapeutically effective amount of trans-[tetrachlorobis(1H-indazole)ruthenate(III)] or a pharmaceutically acceptable salt thereof, preferably an alkali metal salt thereof (e.g., sodium trans-[tetrachlorobis(1H-indazole)ruthenate(III)] or potassium trans-[tetrachlorobis(1H-indazole)ruthenate(III)]).

The term "refractory neuroendocrine tumor" as used herein refers to a neuroendocrine tumor that either fails to respond favorably to an anti-neoplastic treatment that does not include trans-[tetrachlorobis(1H-indazole)ruthenate(III)] or a pharmaceutically acceptable salt thereof, or alternatively, recurs or relapses after responding favorably to an antineoplastic treatment that does not include trans-[tetrachlorobis(1H-indazole)ruthenate(III)] or a pharmaceutically acceptable salt thereof. Accordingly, "a neuroendocrine tumor refractory to a treatment" as used herein means a neuroendocrine tumor that fails to respond favorably to, or resistant to, the treatment, or alternatively, recurs or relapses after responding favorably to the treatment, e.g., a treatment comprising one or more drugs including 5-FU, capecitabine, streptozocin, etoposide, doxorubicin, cisplatin, somatostatin analogs (e.g., octreotide), kinase inhibitors (e.g., sunitinib, crizotinib, everolimus).

To detect a refractory neuroendocrine tumor, patients undergoing initial treatment can be carefully monitored for signs of resistance, non-responsiveness or recurring neuroendocrine tumor. This can be accomplished by monitoring the patient's cancer's response to the initial treatment. The response, lack of response, or relapse of the cancer to the initial treatment can be determined by any suitable method practiced in the art. For example, this can be accomplished by the assessment of tumor size and number. An increase in tumor size or, alternatively, tumor number, indicates that the tumor is not responding to the chemotherapy, or that a relapse has occurred. The determination can be done according to the "RECIST" criteria as described in detail in Therasse et al, *J. Natl. Cancer Inst.* 92:205-216 (2000).

In accordance with yet another aspect of the present invention, a method is provided for preventing, or delaying the onset of, neuroendocrine tumor, or preventing or delaying the recurrence of neuroendocrine tumor, which comprises treating a patient in need of the prevention or delay with a prophylactically effective amount of trans-[tetrachlorobis(1H-indazole)ruthenate(III)] or a pharmaceutically acceptable salt thereof, preferably an alkali metal salt of trans-[tetrachlorobis(1H-indazole)ruthenate(III)] (e.g., sodium trans-[tetrachlorobis(1H-indazole)ruthenate(III)] or potassium trans-[tetrachlorobis(1H-indazole)ruthenate(III)]).

For purposes of preventing or delaying the recurrence of neuroendocrine tumor, patients with neuroendocrine tumor who have been treated and are in remission or in a stable or progression free state may be treated with a prophylactically effective amount of an alkali metal salt of trans-[tetrachlorobis(1H-indazole)ruthenate(III)] (e.g., sodium trans-[tetrachlorobis(1H-indazole)ruthenate(III)] or potassium trans-[tetrachlorobis(1H-indazole)ruthenate(III)]) to effectively prevent or delay the recurrence or relapse of neuroendocrine tumors.

As used herein, the phrase "treating . . . with . . . " or a paraphrase thereof means administering a compound to the patient or causing the formation of a compound inside the body of the patient.

In accordance with the methods of the present invention, in the various embodiments, neuroendocrine tumors may be treated with a therapeutically effective amount of trans-[tetrachlorobis(1H-indazole)ruthenate(III)] or a pharmaceutically acceptable salt thereof, preferably an alkali metal salt of trans-[tetrachlorobis(1H-indazole)ruthenate(III)], alone as a single agent, or alternatively in combination with one or more other anti-cancer agents, chosen from e.g., somatostatin analogs (e.g., octreotide), platinum agents (e.g., cisplatin, carboplatin, oxaliplatin, and picoplatin), taxane (e.g., docetaxel), anthracyclines (e.g., doxorubicin, daunorubicin, epirubicin, idarubicin), 5-FU and prodrugs thereof (e.g., capecitabine, tegafur and S1), nitrosourea compounds (e.g., carmustine (BCNU), lomustine (CCNU), semustine, ethylnitrosourea (ENU) and streptozotocin), gemcitabine, temozolomide, EGFR inhibitors (e.g., erlotinib, gefitinib, cetuximab, panumutimab), sorafenib, regorafenib, crizotinib, everolimus and sunitinib.

Alkali metal salts of trans-[tetrachlorobis(1H-indazole)ruthenate(III)] can be made in any methods known in the art. For example, PCT Publication No. WO/2008/154553 discloses an efficient method of making sodium trans-[tetrachlorobis(1H-indazole)ruthenate(III)].

The pharmaceutical compounds such as sodium trans-[tetrachlorobis(1H-indazole)ruthenate(III)] can be administered through intravenous injection or any other suitable means at an amount of from 0.1 mg to 1000 mg per kg of body weight of the patient based on total body weight. The active ingredients may be administered at once, or may be divided into a number of smaller doses to be administered at predetermined intervals of time, e.g., once daily or once every two days. It should be understood that the dosage ranges set forth above are exemplary only and are not intended to limit the scope of this invention. The therapeutically effective amount of the active compound can vary with factors including, but not limited to, the activity of the compound used, stability of the active compound in the patient's body, the severity of the conditions to be alleviated, the total weight of the patient treated, the route of administration, the ease of absorption, distribution, and excretion of the active compound by the body, the age and sensitivity of the patient to be treated, and the like, as will be apparent to a skilled artisan. The amount of administration can be adjusted as the various factors change over time.

In some embodiments, a pharmaceutically acceptable salt (e.g., an alkali metal salt preferably sodium trans-[tetrachlorobis(1H-indazole)ruthenate(III)]) is administered to a patient at an amount of at least 300, 400, 500, 550, 600, 650, 700 mg/m$^2$ or greater based on body surface area, at each administration. In some embodiments, a pharmaceutically acceptable salt (e.g., an alkali metal salt preferably sodium trans-[tetrachlorobis(1H-indazole)ruthenate(III)]) is administered to a patient at an amount of greater than 600 mg, 700 mg, 800 mg, 900 mg, or 1000 mg at each administration. In preferred embodiments, the drug is administered by intravenous injection once per week, preferably on days 1, 8, and 15 of each 28-day cycle.

In accordance with the present invention, it is provided a use of trans-[tetrachlorobis(1H-indazole)ruthenate(III)] or a pharmaceutically acceptable salt thereof, such as an alkali metal salt of trans-[tetrachlorobis(1H-indazole)ruthenate(III)] (e.g., sodium trans-[tetrachlorobis(1H-indazole)ruthenate(III)] or potassium trans-[tetrachlorobis(1H-indazole)

ruthenate(III)]), for the manufacture of a medicament useful for treating neuroendocrine tumors. The medicament can be, e.g., in an injectable form, e.g., suitable for intravenous, intradermal, or intramuscular administration. Injectable forms are generally known in the art, e.g., in buffered solution or suspension.

In accordance with another aspect of the present invention, a pharmaceutical kit is provided comprising in a container a unit dosage form of trans-[tetrachlorobis(1H-indazole)ruthenate(III)] or a pharmaceutically acceptable salt thereof, such as an alkali metal salt of trans-[tetrachlorobis(1H-indazole)ruthenate(III)] (e.g., sodium trans-[tetrachlorobis(1H-indazole)ruthenate(III)] or potassium trans-[tetrachlorobis(1H-indazole)ruthenate(III)]), and optionally instructions for using the kit in the methods in accordance with the present invention, e.g., treating, preventing, or delaying the onset of, neuroendocrine tumor, or preventing or delaying the recurrence of neuroendocrine tumor, or treating refractory neuroendocrine tumor. As will be apparent to a skilled artisan, the amount of a therapeutic compound in the unit dosage form is determined by the dosage to be used on a patient in the methods of the present invention. In the kit, trans-[tetrachlorobis(1H-indazole)ruthenate(III)] or a pharmaceutically acceptable salt thereof such as an alkali metal salt of trans-[tetrachlorobis(1H-indazole)ruthenate(III)] (e.g., sodium trans-[tetrachlorobis(1H-indazole)ruthenate(III)] or potassium trans-[tetrachlorobis(1H-indazole)ruthenate(III)]) can be in lyophilized form in an amount of, e.g., 25 mg, in an ampoule. In the clinic, the lyophilized form can be dissolved and administered to a patient in need of the treatment in accordance with the present invention.

Example 1

To test the activities of sodium trans-[tetrachlorobis(1H-indazole)ruthenate(III)], ATCC's MTT Cell Proliferation Assay® was performed using human thyroid carcinoma cell line MB1 and Merkel cell carcinoma cell line MKL-1, both being neuroendocrine tumor (NET) cell lines. Stock cultures were allowed to grow to 70-80% confluence for this study. The anti-proliferative activity of sodium trans-[tetrachlorobis(1H-indazole)ruthenate(III)], against the indicated cell line was evaluated in vitro using the ATCC's MTT Cell Proliferation Assay (Catalog No. 30-1010K). The cell plates were seeded with 20E+03 cells/well and treated with sodium trans-[tetrachlorobis(1H-indazole)ruthenate(III)] at 1,000 μM, or a series of 4x dilutions thereof (250 μM, 62.5 μM, etc.). 100 μl of medium was removed from each well at 72 hours post-treatment and 10 μl MTT reagent was added to each well. The plates were incubated plate at 37° C. for 4 hours and then 100 μl of detergent was added. The plates were left overnight at room temperature in the dark and was read on a plate reader using SoftMax® Pro (version 5.2, Molecular Devices).

The absorbance data was analyzed as follows: Absorbance values were converted to Percent of Control and plotted against test agent concentrations for $IC_{50}$ calculations using SoftMax® Pro (version 5.2, Molecular Devices). The plate blank signal average was subtracted from all wells prior to calculating the Percent of Control. Percent of Control values were calculated by dividing the absorbance values for each test well by the No Drug Control average (column 11 values; cells+vehicle control) and multiplying by 100. Plots of Compound Concentration versus Percent of Control were analyzed using the 4-parameter equation to obtain $IC_{50}$ values and other parameters that describe the sigmoidal dose response curve.

The $IC_{50}$ value for the test agents was estimated by curve-fitting the data using the following four parameter-logistic equation:

$$Y = \frac{\text{Top} - \text{Bottom}}{1 + (X/IC_{50})^n} + \text{Bottom}$$

wherein "Top" is the maximal % of control absorbance (100%), "Bottom" is the minimal % of control absorbance at the highest agent concentration (down to zero), Y is the Percent of Control absorbance, X is the test agent Concentration, $IC_{50}$ is the concentration of agent that inhibits cell growth by 50% compared to the control cells, n is the slope of the curve. The $IC_{50}$ values of sodium trans-[tetrachlorobis(1H-indazole)ruthenate(III)] in human thyroid carcinoma cell line MB1 and Merkel cell carcinoma cell line MKL-1 were 73.7 μM and 40.4 μM, respectively.

Example 2

In a human clinical trial conducted in the US, a 51 year old white male with Stage IV Carcinoid tumor of the small bowel (a neuroectodermal tumor or NET) was selected to undergo treatment of sodium trans-[tetrachlorobis(1H-indazole)ruthenate(III)]. He previously had 2 surgeries: an exploratory lap (diagnosis of neuroendocrine tumor) in June 2008, and a partial surgical resection of mass in October 2008. The second surgery was followed by chemoembolization of residual tumor masses for palliative treatment in October 2008 and in November 2008. Systemic chemotherapy with capecitibine was administered between July and August 2009. In August 2009, therapy was changed to octreotide (Sandostatin LAR), but this was discontinued in November 2009. In December 2009, the patient received crizotinib, which was discontinued in March 2010 due to disease progression. The best response to such prior chemo regimens was 1 to 3 months stable disease.

As the tumors were progressing, the patient started therapy on May 7, 2010 with intravenous injection of sodium trans-[tetrachlorobis(1H-indazole)ruthenate(III)] at 320 mg/m$^2$ based on body surface area (for a total dose of 630 mg per administration) once per week, on days 1, 8, and 15 of each 28-day cycle. At that time the patient had four metastatic sites originating from the primary tumor small intestine carcinoid. The four metastatic sites were in portacaval lymph node, left periaortic lymph node, stomach/mesenteric lymph node, and esophageal lymph node. CT scan of the tumors was done at the start of the treatment (baseline), and thereafter every two months. The scanning results are provided in Table 1 below. It can be seen that sodium trans-[tetrachlorobis(1H-indazole)ruthenate(III)] caused almost 50% tumor regression in one lesion, and stopped tumor growth in the remaining three lesions. The patient has received 14 cycles and remains under control on sodium trans-[tetrachlorobis(1H-indazole)ruthenate(III)] as of July 2011. No serious adverse events have been observed.

TABLE 1

The effect of sodium trans-[tetrachlorobis(1H-indazole)ruthenate(III)] in a carcinoid cancer patient*

| Site of metastasis | Pretreatment Baseline# (Apr. 27, 2010) | End of 2$^{nd}$ Cycle (Jun. 24, 2010) | End of 4$^{th}$ Cycle (Aug. 19, 2010) |
|---|---|---|---|
| Portacaval LN | 3.0 | 2.9 | 2.9 |
| Left periaortic LN | 2.5 | 2.5 | 2.5 |

TABLE 1-continued

The effect of sodium trans-[tetrachlorobis(1H-indazole)ruthenate(III)] in a carcinoid cancer patient*

| Site of metastasis | Pretreatment Baseline# (Apr. 27, 2010) | End of 2$^{nd}$ Cycle (Jun. 24, 2010) | End of 4$^{th}$ Cycle (Aug. 19, 2010) |
|---|---|---|---|
| Stomach/mesenteric LN | 3.3 | 3.1 | 3.1 |
| Esophageal LN | 3.8 | 3.0 | 2.0 |

*Size of tumor lesions assessed by CT scan at indicated time points;
Baseline means immediately prior to treatment with sodium trans-[tetrachlorobis(1H-indazole)ruthenate(III)];
LN—lymph node In the same human clinical trial described above, a 70-year old white male with Stage IV gastrinoma of the stomach, (a neuroectodermal tumor or NET) diagnosed in December 2006 was enrolled. He had multiple attempts to achieve disease control with hepatic artery embolization in October 2006, in January 2007, and in September 2007. Localized radiotherapy with Yttrium-90 instillation to the right lobe of the liver in March 2009 and the left lobe in May 2009 was attempted. Yet the tumor was not controlled. In September, 2010, at the time of disease progression, the patient started therapy with intravenous administration of sodium trans-[tetrachlorobis(1H-indazole)ruthenate(III)] at 420 mg/m$^2$ based on body surface area (for a total of 832 mg administered) per week, on days 1, 8, and 15 of each 28-day cycle. The patient received 6 cycles of the drug with best response of stable disease.

Serum gastrin levels were measured using chemiluminescence method during the treatment period. The results are shown in Table 2 below:

TABLE 2

| | Date measured | | | | |
|---|---|---|---|---|---|
| | Sep. 01, 2010 (baseline) | Sep. 30, 2010 | Oct. 28, 2010 | Nov. 29, 2010 | Dec. 28, 2010 |
| Serum gastrin (ng/ml) | 7765 | 8291 | 6881 | 6120 | 8946 |

Note that the serum gastrin level of this patient, the marker of his malignancy, was reduced from 8291 to 6120 during the course of therapy, indicating that the drug was effective in inhibiting tumor growth and reducing tumor marker level.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference. The mere mentioning of the publications and patent applications does not necessarily constitute an admission that they are prior art to the instant application.

Although the foregoing invention has been described in some detail by way of illustration and example for purposes of clarity of understanding, it will be apparent that certain changes and modifications may be practiced within the scope of the appended claims.

What is claimed is:

1. A method of treating neuroendocrine tumor, comprising: administering to a patient diagnosed with neuroendocrine tumor a therapeutically effective amount of a compound that is a pharmaceutically acceptable salt of trans-[tetrachlorobis(1H-indazole)ruthenate(III)].

2. The method of claim 1, wherein said compound is an alkali metal salt of trans-[tetrachlorobis(1H-indazole)ruthenate(III)].

3. The method of claim 2, wherein said compound is sodium trans-[tetrachlorobis(1H-indazole)ruthenate(III)].

4. The method of claim 3, wherein the neuroendocrine tumor is carcinoid tumor.

5. The method of claim 4, wherein the neuroendocrine tumor is carcinoid of the small intestine.

6. The method of claim 3, wherein the neuroendocrine tumor is gastrinoma.

7. The method of claim 3, wherein the neuroendocrine tumor is thyroid carcinoma or Merkel cell carcinoma.

8. The method of claim 3, wherein the neuroendocrine tumor is a refractory neuroendocrine tumor previously treated with a regimen comprising one or more drugs selected from the group consisting of 5-FU, capecitabine, streptozocin, etoposide, doxorubicin, cisplatin, somatostatin analogs, and tyrosine kinase inhibitors.

9. A method of treating neuroendocrine tumor, comprising: identifying a patient having neuroendocrine tumor; and treating the patient with a therapeutically effective amount of a compound that is a pharmaceutically acceptable salt of trans-[tetrachlorobis(1H-indazole)ruthenate(III)].

* * * * *